(12) United States Patent
Torres et al.

(10) Patent No.: US 7,745,161 B2
(45) Date of Patent: Jun. 29, 2010

(54) AMPLIFICATION OF ENZYMATIC REACTIONS FOR USE WITH AN ENTHALPY ARRAY

(75) Inventors: Francisco E. Torres, San Jose, CA (US); Richard H. Bruce, Los Altos, CA (US); James R. Williamson, Del Mar, CA (US); Peter Kuhn, Del Mar, CA (US); Ray Stevens, La Jolla, CA (US)

(73) Assignees: Palo Alto Research Center Incorporated, Palo Alto, CA (US); The Scripps Research Institute, La Jolla, CA (US)

( * ) Notice: Subject to any disclaimer, the term of this patent is extended or adjusted under 35 U.S.C. 154(b) by 1367 days.

(21) Appl. No.: 10/740,776

(22) Filed: Dec. 19, 2003

(65) Prior Publication Data

US 2005/0136392 A1 Jun. 23, 2005

(51) Int. Cl.
*G01N 33/53* (2006.01)
(52) U.S. Cl. .................. 435/7.91; 435/4; 435/194; 435/183; 435/18
(58) Field of Classification Search .............. 435/4, 435/18, 7.91, 194, 184; 374/29, 31
See application file for complete search history.

(56) References Cited

U.S. PATENT DOCUMENTS

| | | | | |
|---|---|---|---|---|
| 3,878,049 | A * | 4/1975 | Tannenbaum et al. | .... 205/777.5 |
| 5,255,976 | A | 10/1993 | Connelly | |
| 5,967,659 | A | 10/1999 | Plotnikov et al. | |
| 6,193,413 | B1 | 2/2001 | Lieberman | |
| 6,380,605 | B1 | 4/2002 | Verhaegen | |
| 6,545,334 | B2 | 4/2003 | Verhaegen | |
| 2003/0044800 | A1* | 3/2003 | Connelly et al. | .............. 435/6 |
| 2003/0183525 | A1 | 10/2003 | Elrod et al. | |
| 2003/0186453 | A1 | 10/2003 | Bell et al. | |

FOREIGN PATENT DOCUMENTS

EP 1 351 052 A2 10/2003

OTHER PUBLICATIONS

Hong Qian et al., "Entropy-enthalpy compensation: Perturbation and relaxation in thermodynamic systems"; *J. Chem. Phys.*, 105(20), Nov. 22, 1996, pp. 9292-9298; © 1996 American Institute of Physics.

"Introduction to the GPCR and GPCR pathway"; http://ressell.postech.ac.kr/~project/Research/POSBIOTM/content/intro.html, Dec. 5, 2003, 6 pgs.

Brian F. King et al., "Nucleotide and Nucleoside Receptors", *Tocris Reviews* No. 23, Mar. 2003, pp. 1-12; © 2003 Tocris Cookson.

Johannessen, Erik A., et al., *Micromachined Nanocalorimetric Sensor for Ultra-Low-Volume Cell-Based Assays*; © 2002 American Chemical Society; Analytical Chemistry, vol. 74, No. 9, May 1, 2002; 2002 American Chemical Society, pp. 2190-2197.

Johannessen, Erik A. et al., *Heat Conduction Nanocalorimeter for PL-Scale Single Cell Measurements*, © 2002 American Institute of Physics, Applied Physics Letters, vol. 80, No. 11, Mar. 18, 2002, pp. 2029-2031.

Verhaegen, Katarina, et al., *A High-Throughput Silicon Microphysiometer*, © 2000 Elsevier Science S.A., Sensors and Actuators 82 (2000), pp. 186-190.

Klinov, Sergey, et al., *Kinetic Mechanism of Activation of Muscle Glycogen Phosphorylase b by Adenosine 5'-Monophosphate*; © 1994 Academic Press, Inc., Archives of Biochemistry and Biophysics, vol. 312, No. 1, Jul. 1994, pp. 14-21.

Kengen, Serve W., et al., *Purification and Characterization of a Novel ADP-Dependent Glucokinase From the Hyperthermophilic Archaeon Pyrococcus Furiosus*; © 1995 by The American Society for Biochemistry and Molecular Biology, Inc., The Journal of Biological Chemistry, vol. 270, No. 51, Dec. 22, 1995, pp. 30453-30457.

McLaughlin, John, et al., *Inorganic Pyrophosphatase and Nucleoside Diphosphatase in the Parasitic Protozoon, Entamoeba Histolytica*; © 1978 Academic Press, Inc., Biochemical and Biophysical Research Communications, vol. 82, No. 3, Jun. 14, 1978, pp. 913-920.

Chalmers, Derek T., et al., *The Use of Constitutively Active GPCRS in Drug Discovery and Functional Genomics*; © 2002 Nature Publishing Group., Aug. 2002, vol. 1, No. 8, http://www.nature.com/cti-taf/DynaPage.taf?file+/nrd/i..., Aug. 30, 2004, pp. 1-15.

Milligan, Graeme, *High Content Assays for Ligand Regulation of G-Protein-Coupled Receptors*; © 2003 Elsevier Science Ltd., Drug Discovery Today, vol. 8, No. 13, Jul. 2003, pp. 579-585.

(Continued)

*Primary Examiner*—Sandra Saucier
*Assistant Examiner*—Susan Hanley
(74) *Attorney, Agent, or Firm*—Fay Sharpe LLP

(57) ABSTRACT

Provided is a method of detecting characteristics of a reaction of interest, including instituting the reaction of interest, obtaining an amplified heat related to the reaction of interest, measuring the amplified heat, and determining the characteristics of the reaction of interest, using the signal obtained in the step of measuring.

27 Claims, 6 Drawing Sheets

OTHER PUBLICATIONS

Pancera, S.M., et al.: "The effect of poly(ethylene glycol) on the activity and structure of glucose-6-phosphate dehydrogenase in solution"; *Colloids and Surfaces*, 'Online!, vol. 26, 2002, pp. 291-300, XP002320528, Retrieved from the Internet: URL:http://pcserver.iqm.unicamp.br/{wloh/pu2002-4.pdf<.

Johannessen, E.A., et al.: "A suspended membrane nanocalorimeter for ultralow volume bioanalysis"; *IEEE Transactions on Nanobioscience*, IEEE Service Center, Piscataway, NY, US; vol. 1, No. 1, Mar. 1, 2002, pp. 29-36, XP002294495; ISSN: 1536-1241.

The Calorimetry Experts: "Use of Isothermal Titration Calorimetry to Measure Enzyme Kinetics Parameters"; ITC Application Note, 'Online! 2003, pp. 1-6, XP002320529; Retrieved from the Internet: URL:http://www.microcalorimetry.com/files/enzymekineticsappnote.pdf>; Retrieved on Mar. 8, 2005.

-& Microcal Application Notes and Technical Data Sheets; 'Online! XP002320640; Retrieved from the Internet: URL:http://web.archive.org/web/20031225091315/www.microcalorimetry.com/index.php?id=48> 'Retrieved on Mar. 8, 2005.

Torres, Francisco E., et al.: "Enthalpy arrays"; Proceedings of the National Academy of Sciences of the United States of America; Jun. 29, 2004, vol. 101, No. 26, Jun. 29, 2004, pp. 9517-9522, XP00232530; ISSN: 0027 8424.

Fersht, A., *Structure and Mechanism in Protein Science*, W. H. Freeman & Co., N. Y., 1999, p. 309-310.

Hellman, F., "Development of Instrumentation for Microcalorimetry of Biological Systems", *NSF Award Abstract*, #9513629 AWS FL008-DS3 (4 pgs.).

Beeley, Nigel R.A. et al., "GPCRs: An Update on Structural Approaches to Drug Discovery", *Targets*, vol. 2, Feb. 2003, 19-25.

Scott, L.G. et al., "Preparation of specifically $^2$H- and $^{13}$C-labeled ribonucleotides", *Methods of Enzymology*, 2000, 317:18-38.

Wilson, S. et al., "Orphan G-Protein Coupled Receptors: Novel Drug Targets for the Pharmaceutical Industry", *Drug Design & Discovery*, 2000, vol. 17, Issue 2, pp. 105-114.

Hellman, F., "Development of Instrumentation for Microcalorimetry of Biological Systems", *NSF Award Abstract*, #9513629 AWS FL008-DS3 (4 pgs.). Aug. 18, 2006.

* cited by examiner

AMPLIFICATION OF ENZYMATIC REACTIONS FOR USE WITH AN ENTHALPY ARRAY

BACKGROUND

The present development relates to systems and methods for monitoring chemical reactions using calorimetry and enthalpy arrays, and specifically to systems and methods which use enzymes to amplify the reactions.

BACKGROUND

Calorimetry is used to measure enthalpic changes, including enthalpic changes arising from reactions, phase changes, changes in molecular conformation, temperature variations, and other variations of interest that may occur for a particular specimen. By measuring enthalpic changes over a series of conditions, other thermodynamic variables may be deduced. For example, measurements of enthalpy as a function of temperature reveal the heat capacity of a specimen, and titrations of reacting components can be used to deduce the equilibrium constant and effective stoichiometry for a reaction. Calorimetry measurements are useful in a broad variety of applications, including, for example, pharmaceuticals (drug discovery, decomposition reactions, crystallization measurements), biology (cell metabolism, drug interactions, fermentation, photosynthesis), catalysts (biological, organic, or inorganic), electrochemical reactions (such as in batteries or fuel cells), and polymer synthesis and characterization, to name a few. In general, calorimetry measurements can be useful in the discovery and development of new chemicals and materials of many types, as well as in the monitoring of chemical processes. It is understood that an enthalpy array may be considered an array of calorimeters (e.g., nanocalorimeters).

Calorimeters and enthalpy arrays can, therefore, be used to screen for substrates, cofactors, activators, and inhibitors of enzymes, including at the proteome level, and can also be used to quantify the enzymatic kinetics. Calorimeters/enthalpy arrays detect the amount of heat evolved from an enzymatic reaction. The heat evolved depends on the enthalpy of the reaction, enzyme concentration, substrate concentrations, the presence of inhibitors, activators, or cofactors, values for the kinetic parameters for the reaction of interest, buffer conditions, as well as various other factors and parameters. In particular, the concentrations of the enzyme, one or more substrates, and/or regulators (e.g. agonists, inhibitors, and inverse agonists) are often a limiting factor in analyzing enzymatic reactions by detecting the enthalpy of reaction. Specifically, it is often necessary to use low concentrations of enzyme and/or substrates when examining enzymatic reactions, yet at the low concentrations of interest, the amount of heat evolved is low.

One benefit of low concentration studies is that the use of smaller concentrations provides for more selective reactions. Consider, for example, the study of a binding reaction with a dissociation constant $K_d$:

$$A + B \rightarrow C$$
$$K_d = \frac{[A][B]}{[C]}$$

In this reaction, A and B bind to form the complex C, and the dissociation constant is written in terms of concentrations denoted by square brackets. This equation assumes ideal solution behavior, but it is sufficient for the purposes herein. In testing for binding, it is often desired to obtain an indication of the magnitude of $K_d$. In many biochemical studies, including drug screening and development studies and proteome-wide investigations of protein-protein interactions, among others, $K_d$ values of interest are typically <1-10 μM, and values from 1-1000 nM—and especially <100 nM—are not uncommon and often of particular interest. In order to measure $K_d$, the reaction must be studied at concentrations that are not too distant from the value of $K_d$. At the upper end of this range, titrations may be performed at concentrations of 10 to 100 times $K_d$, but titrations at concentrations near the value of $K_d$ are preferred when possible. Thus, there is a benefit to performing studies at as low a concentration as possible. In particular, there is a benefit to being able to perform studies at concentrations as low as $10^{-6}$ to $10^{-7}$ M. Likewise, it is a benefit to be able to measure kinetics of enzymatic reactions at low concentrations, including enzymatic reactions with slow turnover rates.

It is also useful to work with substrates at low concentrations. In analyzing enzymatic reactions, benefits arise from determining the Michaelis constant, $K_m$, which provides an indication of the substrate concentration at which an enzyme is most effective at increasing the rate of reaction. If the concentration of the substrate needs to be increased beyond the $K_m$ for that substrate, it then becomes difficult or impossible to accurately determine $K_m$ using calorimetry. Measuring reactions at lower concentrations allows one to differentiate, e.g. strong binding from weaker binding, or larger $K_m$ in the case of enzymatic reactions from smaller $K_m$, etc.

Likewise, in drug screening studies, reaction information at lower concentrations is often necessary to determine binding constants, for example, or to differentiate strongly binding hits in drug screening campaigns from hits that do not bind as strongly. The concentrations used in the experiments will then set the lower limits of reactions that are being distinguished. It is therefore advantageous to work at low concentrations in a variety of areas, including but not limited to drug screening and biochemical research.

In addition to the needs for using low concentrations, it is also important in many studies to use as small a volume of materials as possible, since the combination of small volume and low concentration means small amounts of the materials of interest. The amount of sample, e.g. purified enzyme or other protein, is often limited, and making the samples is often labor intensive and costly. Additionally, the quantity of desired experiments may require the use of low concentrations and small volumes. In drug screening or proteome scale experiments, for example, researchers may be running anywhere from 1,000 to 100,000 or more different experiments. Also, one may desire to study a natural extract or synthesized compound for biological interactions, but in some cases the available amount of material at concentrations large enough for calorimetry might be no more than a few milliliters. The use of enzymes and/or substrates in such studies can only be kept within a tolerable range if sample concentrations and volumes are kept as low as possible. In particular, performing such studies is not feasible using sample sizes of about 1 ml, as required for measurement using commercially available microcalorimeters such as products sold, for example, by MicroCal® Inc. (model VP-ITC) or Calorimetry Sciences Corporation® (model CSC4500).

In certain situations, the enzymatic reactions of interest, at the low concentrations and small volumes required by many studies, may not generate a sufficient amount of heat to be reliably detected by calorimetric methods. Thus, using small quantities of materials may not yield a signal and prevents researchers from monitoring the reactions. It would, therefore, be advantageous to provide a method for monitoring enzymatic reactions using calorimetric measurements and/or enthalpy arrays that allows researchers to operate and perform experiments within the boundaries in which they are required to work, including limitations in concentration and sample volume. In that regard, it would be a further advantage to provide a method for monitoring enzymatic reaction via, calorimetry and/or enthalpy arrays using low concentrations and small volumes of enzymes, substrates, activators, regulators, inhibitors and/or co-factors.

Binding of ligands, such as agonists, inverse agonists, or inhibitors, to GPCRs (G-protein coupled receptors) is an example of a reaction that may not produce a sufficient amount of heat to be reliably detected using a desired calorimetric method. It may be desirable in drug screening applications to test for binding of library compounds to GPCRs by high throughput calorimetry, using arrays of calorimeters such as those described in, U.S. application Ser. No. 10/114,611, filed Apr. 1, 2002, titled "Apparatus and Method for a Nanocalorimeter for Detecting Chemical Reactions"; U.S. Pat. Nos. 6,380,605 B1 and 6,545,334 B2, each entitled, "Device and a Method for Thermal Sensing", to Verhaegen; U.S. Pat. No. 6,193,413, entitled, "System and Method for an Improved Calorimeter for Determining Thermodynamic Properties of Chemical and Biological Reactions", to Lieberman; Johannessen, et al., Applied Physics Letters, vol 80(11): 2029-2031; Johannessen, et al., Analytical Chemistry A 2002 May 1; 74(9):2190-7; K. Verhaegen, et al., Sensors and Actuators 82(2000):186-190; and F. Hellman, NSF Award Abstract—#9513629 AWSFL008-DS3: "Development of Instrumentation for Microcalorimetry of Biological Systems". However, preparing samples with a high enough GPCR concentration to yield a detectable signal in such systems can be difficult or even impractical, in part because the cost of expressing GPCRs in the desired amounts is large and in part because GPCRs are membrane proteins. Membrane proteins can be provided in suspensions of cell membranes, membrane fragments, vesicles, or micelles, but they are only a part of the membranes, fragments, vesicles, or micelles, which makes increasing the concentration more challenging than for soluble proteins.

GPCRs are one of the most important classes of protein targets for the pharmaceutical industry. GPCR's are membrane proteins involved in signaling cells based on extracellular signaling molecules, and approximately 50% of the top 200 drugs currently on the market target GPCRs. Today, GPCRs with known ligands are screened by measuring how test compounds affect the behavior of the GPCR, using assays that include the known ligand. Accordingly, traditional drug screening for GPCR targets has relied on the identification of small molecules that interfere with binding of a know ligand to the GPCR, as described in "The Use of Constitutively Active GPCRS in Drug Discovery and Functional Genomics", Derek T. Chalmers & Dominic P. Behan, *Nature Reviews Drug Discovery* 1, 599-608 (2002). The situation for orphan GPCRs, which do not have known ligands, is more complicated. In an article on assays for ligand regulation of orphan GPCRs (*Drug Discovery Today* vol. 8, No. 13, July 2003, pp. 579-585) by G. Milligan, the author states that efforts to identify ligands that interact with orphan GPCRs have shifted from ligand-binding assays to functional assays because it is currently impossible to perform binding assays in the absence of a known ligand. Methods for screening for ligands of orphan GPCRs use cellular assays that involve fluorescent tagging, hypotheses about cellular behavior of the GPCRs, and possibly modifying the GPCR itself, e.g. to make it constitutively active. Examples include AequoScreen™ technology from Euroscreen, which is based on using fluorescent reporters of Ca+2 activity in cellular assays, Ca+2 changes being a common result of GPCR activity, and CART Constitutively Activating Receptor Technology (CART), described in an article in, "*Nature Reviews Drug Discovery* 1, 599-608 (2002); "The Use of Constitutively Active GPCRS in Drug Discovery and Functional Genomics", by Chalmer and Behan, which is based on modifying GPCRs to make them constitutively active and using these GPCRs in cellular assays. These methods do not directly detect ligand binding to a GPCR or the associated G-protein activity. A method that directly probes ligand binding to a GPCR without requiring an assay based on a previously known ligand would be very useful. In particular, a calorimetric method would be very useful, especially if it could be used with arrays of calorimeters that enable parallel measurements at appropriate concentrations and with small amounts of material for each measurement.

Similarly, calorimetric studies of kinases, proteases, ion channels, phosphatases, metabolic enzymes, nucleic acid binding and modifying enzymes, transcription/translation factors, signaling enzymes, protein modifying enzymes, transport/trafficking enzymes, and orphan enzymes are all of potential benefit in biological research and drug discovery activities, especially if they could be performed with arrays of calorimeters that enable parallel measurements at appropriate concentrations and with small amounts of material for each measurement.

BRIEF DESCRIPTION

Provided is a method of detecting characteristics of a reaction of interest, including instituting the reaction of interest, obtaining an amplified heat related to the reaction of interest, measuring the amplified heat, and determining the characteristics of the reaction of interest using the signal obtained in the step of measuring.

In one aspect, a method is provided for monitoring enzymatic reactions by the enthalpy of such reactions. The method includes conducting a primary reaction comprising the reaction of a subject enzyme with one or more subject compounds. The primary reaction produces one or more enzyme specific products and generates heat. The method also includes amplifying the heat generated from the primary reaction to produce a sufficient amount of heat that is capable of detection.

In another aspect, a method for monitoring enzymatic reactions by the enthalpy of such reactions includes conducting a primary reaction comprising the reaction of a subject enzyme and one or more subject compounds. The primary reaction produces one or more enzyme specific products and evolves heat. The method further includes amplifying the heat evolved from the primary reaction by initiating a secondary reaction cascade that evolves heat. The heat from the secondary reaction cascade adds to the heat of the primary reaction to produce a sufficient amount of heat capable of being detected by a detector. The method also includes detecting the heat from the primary reaction and the secondary reaction cascade.

In still another aspect, a method for monitoring enzymatic reactions by the enthalpy of such reactions is provided wherein the heat generated from a primary reaction between a subject enzyme and one or more subject compounds is amplified by initiating a secondary reaction cascade. The secondary reaction cascade includes an amplification reaction catalyzed by an amplifying enzyme. The amplification reaction evolves heat. The heat from the primary reaction, in the absence of the amplification reaction does not produce a sufficient amount of heat to be detectable at a desired level of sensitivity. That is, amplification may provide an increased signal and a more favorable signal to noise ratio and, therefore, increased precision. The heat from the secondary reaction cascade adds to the heat of the primary reaction, and this heat is detected by a detector.

In yet another aspect, an enthalpy array device for monitoring enzymatic reactions is provided. The device comprises a means for conducting a primary reaction. The primary reaction includes reacting a subject enzyme with one or more subject compounds to produce one or more enzyme-specific products. The primary reaction generates a first amount of heat. The device also includes a means for amplifying the heat from the primary reaction to produce an amplified amount of heat capable of detection.

BRIEF DESCRIPTION OF THE DRAWINGS

The present development may be more readily understood when read in reference to the following figures.

DETAILED DESCRIPTION

As used herein, the terms "amplification", "amplify", "amplified heat", and derivatives thereof refer to increasing the amount of heat generated in a sample when a specific reaction of interest, also referred to as the "primary reaction", occurs in the said sample. The increased amount of heat is in addition to the heat generated directly by the enthalpy of the specific reaction of interest. The primary reaction can be exothermic, endothermic, or have zero enthalpy of reaction, and still undergo amplification as defined here. Insofar as the purpose of amplification is to increase the magnitude of the thermal event, the term "amplification" can also be used to describe the increase in the amount of heat absorbed, i.e. the amount of cooling, when the amplification is endothermic rather than exothermic.

Figure 1:
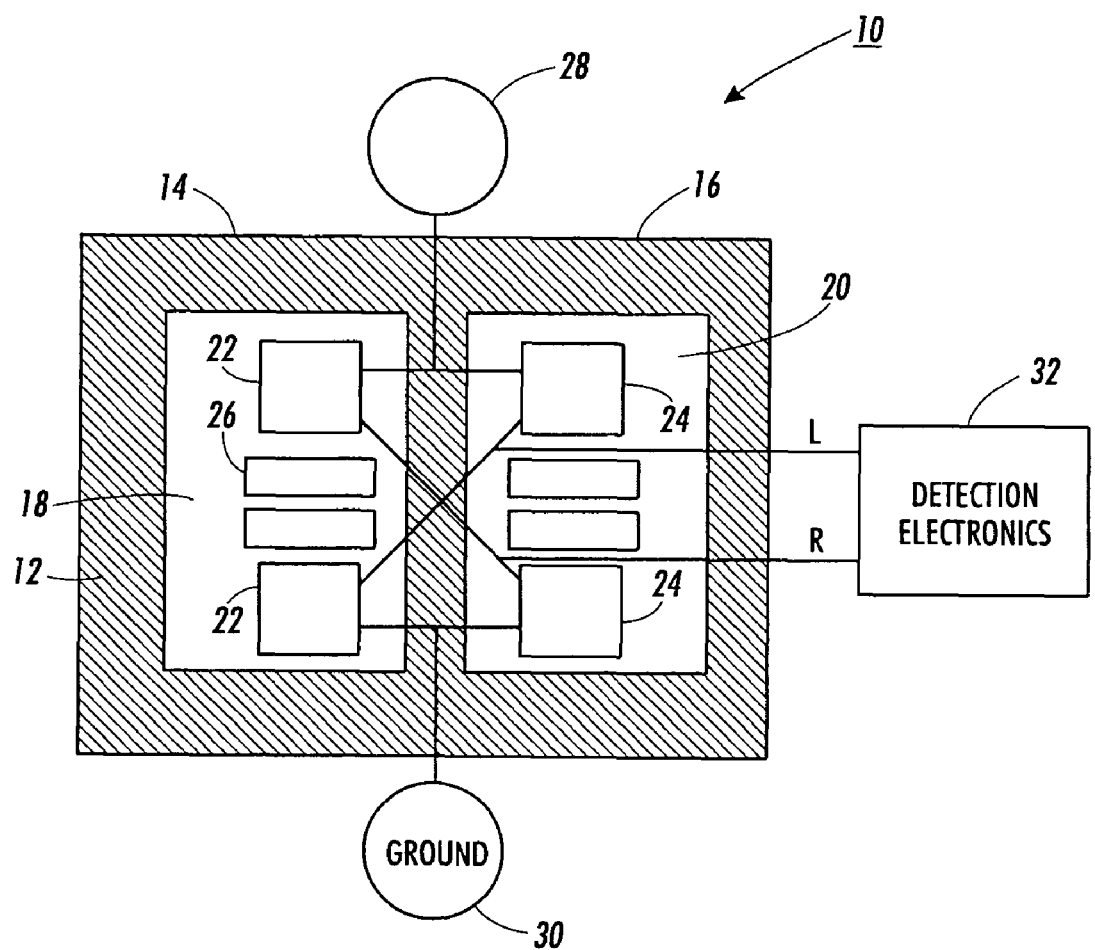
FIG. 1 is a block diagram depicting components of a nanocalorimeter device/apparatus in which the present method may be implemented.

While the description of the following method is not intended to be limited, a particular calorimeter to which this application may be applied, is the nanocalorimeter described in U.S. application Ser. No. 10/114,611, and illustrated herein, in one embodiment, in FIG. 1. Nanocalorimeter 10 includes thermal isolation layer 12, which contains measurement region 14 and reference region 16. Regions 14 and 16 may also be contained in separate isolation regions, as described hereinbelow. Thermal isolation region 12 provides isolation from surrounding thermal environments, thus increasing measurement time and reducing thermal noise. Although layer 12 is used in this example embodiment to thermally isolate the reaction and temperature sensing components of the nanocalorimeter 10, any means to thermally isolate these components can be used in alternate embodiments of the present invention.

In this example embodiment, the thermal isolation layer 12 may comprise a plastic material in thin foil form (typically ranging from less than 12.5 microns to approximately 25 microns in thickness for this embodiment and as thin as 2 microns and as thick as 500 microns for other applications). Candidate plastic materials include polyimide (for example Dupont Kapton® and others), polyester (for example Dupont Mylar®) foil, PolyEtherEtherKetone (PEEK), or PolyPhenylene Sulphide (PPS). Alternatively, in embodiments, the thermal isolation region comprises other thin membranes of sufficiently low thermal conductivity, such as SiN and comparable materials.

Measurement region 14 and reference region 16 include thermal equilibrium regions 18 and 20 respectively, that are thermally isolated from the detector's mechanical support. In this example embodiment, thermal equilibrium region 18 contains two resistive thermometers 22, which measure the reaction temperature, while thermal equilibrium region 20 contains a second set of two thermometers 24, which measure the variations in the background temperature. The resistive thermometers are deposited in thermal equilibrium regions 18 and 20 using standard fabrication techniques, including in embodiments, but not limited to, lithographic patterning of thin films, micro-electronic fabrication techniques (e.g. including sputtering, chemical etching, evaporation), and printed circuit board fabrication techniques. Both thermal equilibrium regions 18 and 20 are sufficiently large to receive and support separate drops of protein and ligand deposited by direct printing and also to support the combination of these two drops after merging, triggered by an example drop merging device 26. An example of a drop merging system is shown in U.S. application Ser. No. 10/115,336, filed Apr. 1, 2002, titled "Apparatus and Method for Using Electrostatic Force to Cause Fluid Movement", fully hereby incorporated herein by reference. For example, for a 400 nL final drop size, the detector, which includes the measurement and reference regions, may be 3.7 mm by 4.6 mm. Each thermal equilibration region 18 and 20 has a sufficient thermal conduction for the region to equilibrate quickly relative to the thermal dissipation. The regions have a sufficiently low heat capacity such that little of the heat of reaction is absorbed in the support.

As suggested above, the thermal equilibration regions must be thermally isolated from their environment so that the temperature difference caused by the reaction takes a relatively long time to dissipate. The longer this dissipation time, the longer the signal can be integrated during measurement, which improves the signal to noise ratio.

Each thermal equilibration region 18 and 20 contains thermometers 22, 24 and drop merging electrodes 26. Although for the purposes herein thermometers 22, 24 are shown spaced apart from more centrally-positioned drop merging electrodes 26 on each thermal equilibration region 18 and 20, this configuration is for means of example only. Provided that the drop merging device 26 and thermometers 22, 24 are in good thermal contact with the high conductance film, the exact placement of thermometers 22, 24 and drop merging electrodes 26 is not important for thermal considerations.

In operation, the two resistive thermometers 22 situated in thermal equilibration region 18 detect the heat of reaction in drops deposited within thermal equilibration region 18. The drops may contain enzymes together with substrate(s) and any necessary cofactors, proteins, ligands, or any other compounds that are expected to be necessary for the solution to undergo an enthalpic change upon mixing. In this example, the heat of reaction is detected through measurement of a voltage change in a bridge circuit due to the resistance change in the thermometers which are configured in the bridge circuit. Resistive thermometers 22 in thermal equilibrium region 18 detect a reaction between a sample ligand and a protein (or enzyme-substrate); the other resistive thermometers 24 in thermal equilibrium region 22 serve as a reference. Because the temperature rise due to the reaction may be small, the resistive thermometers 22 and 24 are fabricated from materials that provide a large change in resistance for a small temperature change.

Resistive thermometers 22, 24 are configured as an AC bridge driven by AC generator 28 and ground 30, discussed in more detail hereinbelow. After the drops have reached thermal equilibrium, they are moved together to initiate the reaction. The movement operation creates sufficient mixing of the two drops in a time small compared to the measurement time. The heat released by the protein-ligand (or enzyme-substrate) reaction of the test combination causes a change in the resistance of the affected thermometers relative to the reference thermometers. This change in resistance causes the voltage at the detection point to change. The output reactions are then detected by detection electronics 32. This change is then detected by sensitive, noise rejecting circuits, such as circuits or systems comprising a lock-in amplifier.

An advantage of using nanocalorimeters and arrays of nanocalorimeters, including the nanocalorimeter described above, is the ability to keep sample volumes, and therefore sample consumption, low. In particular, measurements of both binding and enzymatic reactions using the above nanocalorimeter have been demonstrated using sample volumes of about 200-250 nL. This is of great significance when it is difficult to obtain a material to be studied and when a large number of studies, such as screening against a large library of compounds, are to be performed. Enabling a large number of measurements provides the ability to approach studies using high throughput strategies, thereby enabling extensive investigations that would not otherwise be possible. By providing for amplification of the heat from reactions that might otherwise evolve too little heat for detection by a nanocalorimetric, small volume measurement, this invention extends the range of measurements that can be performed with nanocalorimeters at small volumes. Specifically, this invention is particularly useful in the range of sample volumes of 50-600 µL and below, and especially below about 30 µL, which are typical of the upper end of sample volumes cited in literature on nanocalorimeters, including U.S. application Ser. No. 10/114,611, filed Apr. 1, 2002, titled "Apparatus and Method for a Nanocalorimeter for Detecting Chemical Reactions", U.S. Pat. No. 6,380,605 B1, U.S. Pat. No. 6,545,334B2, and the article by K. Verhaegen, et al. (Sensors and Actuators 82(2000)):186-190). Further, the invention extends the range to sample sizes as small as 1 microliter, and even as small as 300 nanoliters.

Figure 2A:
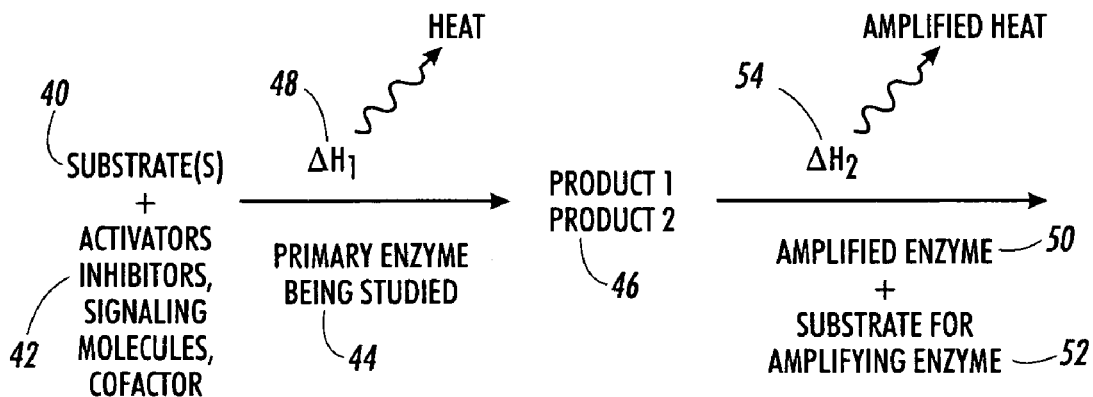
FIG. 2A is a schematic of a general scheme of a method for amplifying the heat generated from an enzymatic reaction.

Turning attention to FIG. 2A, the concepts of present exemplary embodiments are directed to methods for monitoring chemical and/or biochemical reactions, and, in particular, the reaction of test or subject enzymes and test compounds using a calorimeter or enthalpy array. The test compounds are generally a substrate and enzyme, together with any test activator, inhibitor, cofactor, or the like. The test compounds may be provided in a mixture prepared from the components, or they may also be provided from preparations of whole cells, cell extracts, or any other non-purified mixtures. Examples of test or subject enzymes include kinases, proteases, ion channels, phosphatases, metabolic enzymes, nucleic acid binding and modifying enzymes, transcription/translation factors, signaling enzymes, protein modifying enzymes, transport/trafficking enzymes, GTPases, GPCRs, and G-proteins, and orphan enzymes. It is to be understood that this list is not intended to be exhaustive, but rather any enzyme which would provide information of interest may be a test or subject enzyme appropriate for the present concepts. The reaction products generally include one or more enzyme-specific products and/or one or more other products (i.e., non enzyme-specific products). For example, ATP kinase reactions will produce a kinase-specific phosphorylated product (depending on the substrate specificity for the ATP kinase) and ADP. It will be appreciated that the method may be used to monitor a chemical reaction that may not produce detectable quantities of heat at low concentrations. In addition, amplification is also useful where the heat of a reaction may be detectable, but the sensitivity of the measurement is not sufficient to render the information/data useful, e.g., where there is a low signal-to-noise ratio. Amplification may increase the signal and improve the signal-to-noise ratio to allow for greater precision in detection.

The monitoring method includes amplifying the heat generated by a subject enzymatic reaction. With continuing reference to FIG. 2A, a general method for amplifying heat generation from subject enzymatic reactions is shown. Initially, an appropriate substrate(s) 40 is combined with primary enzyme and any activators, inhibitors, other signaling molecules or cofactors 42 that are required for the specific reaction of interest, or are being investigated as to their effect on the reaction of interest. This action causes a primary reaction 44. The primary reaction comprises one or more enzymatic reactions involving a subject (or primary) enzyme and/or subject or test compounds being studied to yield one or more reaction products 46. The primary reaction generates heat $(\Delta H_1)$ 48.

Following the primary reaction, the heat from the primary reaction is amplified. The primary reaction is amplified by initiating a secondary reaction cascade, by a process of combining an amplifying enzyme 50 and a substrate 52 for the amplifying enzyme. The secondary reaction cascade can be a naturally occurring event or series of events engineered properly for the purposes of these embodiments, or it can be a designed event or series of events that does not occur naturally. The secondary reaction cascade includes additional downstream reactions that also evolve an amplified heat $(\Delta H_2)$ 54. Heat 54 from the downstream reactions adds to the heat 48 generated from the primary reaction. A detector, such as a calorimeter and/or enthalpy array is provided to detect the primary heat 48 and amplified heat 54. Amplifying the heat from the primary reaction provides a greater quantity of heat than is obtained from the primary reaction alone. Consequently, the amplified heat 54 and the primary heat 48 produces a larger signal, when measured by a calorimeter or other suitable device, than would be obtained from the primary enzymatic reaction alone.

The secondary reaction cascade includes amplification materials, i.e., amplifying enzyme 50 and substrate 52, in sufficiently high concentrations such that a sufficient amount of heat is produced to generate the desired amplification of the heat signal. Generally, in the secondary reaction cascade, the amplifying enzyme 50 is combined with the substrate 52 such that an enzymatic reaction, i.e., an amplification reaction, occurs and produces amplifying heat 54 which is an amplification of the primary reaction. In one embodiment, the amplification reaction of the secondary reaction cascade occurs when the amplifying enzyme is activated or agonized, directly or indirectly, as a result of the production of one or more of the products 46 of the primary reaction. As used herein, activation of an enzyme includes agonization or agonizing an enzyme. In another embodiment, the amplification reaction diminishes when the amplifying enzyme is inhibited, directly or indirectly, by a product of the primary reaction.

In addition to the amplification reaction, the secondary reaction cascade may involve a series of additional reactions. As previously mentioned, the product(s) 46 of the primary reaction initiates the secondary reaction cascade. For example, one or more products can be further processed in a linear way to release additional heat. Specifically, one or more products 46 in FIG. 2A can act as the substrate 52 for one or more amplifying enzymes 50. In other embodiments, one or more products bind to and activates, or inhibits, an amplifying enzyme that can act on a large reservoir of a different substrate. The binding could be allosteric activation, allosteric or competitive inhibition, or it could provide a catalytic cofactor required for activity, as examples. In yet other embodiments, one or more products could act as a substrate for modifying an inactive enzyme to the active form, an example being a cascade in which a kinase activates another kinase by phosphorylating it, using a nucleotide from the primary reaction. In further embodiments, combinations of the above methods are used together, including embodiments in which enzyme cascades are used in succession to amplify in two or more stages.

When the amplification reaction is driven forward by the activation or agonization of the amplifying enzyme 50, the amplifying enzyme is activated or agonized either directly or indirectly by the product of the primary reaction. In direct activation or agonization, a product directly activates or agonizes the amplifying enzyme. In indirect activation, a product of the primary reaction is converted into a species that activates or agonizes the amplifying enzyme. Thus, under indirect activation or agonization, the secondary reaction cascade comprises one or more reactions that convert a product of the primary reaction into a species that activates or agonizes the amplifying enzyme.

The reaction product that initiates the secondary reaction cascade may be either an enzyme-specific product or another product of the primary reaction. The secondary reaction cascade may be initiated by at least one of the one or more enzyme-specific products of the primary reaction. When the secondary reaction cascade is initiated by an enzyme-specific product, the enzyme-specific product may activate the amplifying enzyme 50 directly, or the enzyme-specific product may be converted into a species that can activate the amplifying enzyme. To convert an enzyme-specific product to a species that is capable of activating or agonizing the amplifying enzyme 50, the reagents necessary to complete such a conversion are provided. The conversion of an enzyme-specific product into an activating species may include a series of enzymatic reactions.

Alternatively, the amplifying enzyme 50 may be directly or indirectly activated by a product of the primary reaction other than an enzyme-specific product. For example, another product of the primary reaction may directly activate the amplifying enzyme. Additionally, another product of the primary reaction may be converted, via one or more enzymatic reactions, to a species that activates the amplifying enzyme.

Once the amplifying enzyme 50 is activated or agonized, another enzymatic reaction, i.e., the amplification reaction, occurs between the amplifying enzyme 50 and substrate 52 for the amplifying enzyme that produces heat. Preferably, substrate 52 for amplifying enzyme 50 is provided at a concentration sufficient for the process. The heat from the amplification reaction amplifies the heat 48 generated from the primary reaction. The amplified heat 54 provides a sufficient amount of heat that is capable of detection by a calorimeter or enthalpy array.

Figure 2B:
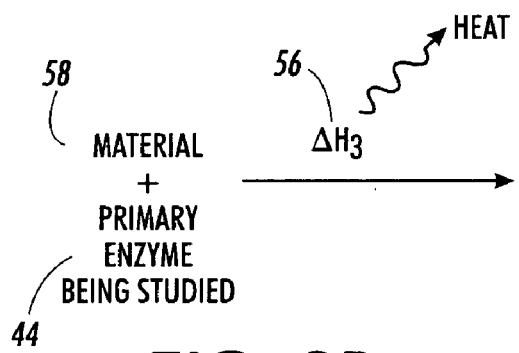
FIG. 2B is a schematic of a general scheme of an alternative method for amplifying heat.

It is to be appreciated from FIG. 2B that under appropriate circumstances, i.e., with appropriate materials and test parameters, an amplified heat ($\Delta H_3$) 56 may be obtained by the binding of a material (such as molecules, including for example proteins that increase the activity of the primary enzyme under suitable conditions) 58 to the primary enzyme 44. It is to be understood that in this embodiment the use of the term "amplified heat" is intended to mean that it is a heat greater than has otherwise been obtainable from the subject enzyme prior to application of this technique. Therefore, the commonality of the term amplified heat, as used in FIGS. 2A and 2B is the concept of obtaining a greater amount of heat from a related enzyme than previously obtainable. Amplified heat 56 is then used to detect changes in the primary enzymatic reaction caused by the materials binding to the primary enzyme, such as activators, inhibitors, signaling molecules, and cofactors. Accordingly, an alternative method of amplifying the heat is shown which can be used to study binding of materials to the primary enzyme. This method can, for example, be used for screening of a library for agonists or inhibitors, including protein species that may themselves require a ligand to act as an agonist or inhibitor. The method of amplifying the heat from the primary reaction can also be used to study the turnover of substrates, or potential substrates. For example, experiments at different concentrations of substrates can be used to determine kinetic parameters, and screening experiments with different candidate substrates can be used to find surrogate substrates for enzymes. Finding surrogate substrates can be particularly useful when the primary enzyme is an orphan enzyme, i.e. one with an unknown substrate but a predicted function. Orphan kinases or phosphatases determined from a genome are examples of such enzymes.

Any enzyme capable of generating a sufficient amount of heat to amplify the heat 48 generated by the primary reaction is suitable for use with the method(s) described herein. Similarly, a given amplifying enzyme may serve to provide amplified heats for many different primary reactions, limited only by the ability to couple the two. Preferably, an amplifying enzyme is capable of adopting two states: 1) a tightly regulated inactive state, and 2) a highly activated state. Non-limiting examples of enzymes suitable for use as an amplifying enzyme include phosphorylase b, phosphofructokinase, isocitrate dehydrogenase, and pyruvate kinase. Phosphorylase b is particularly suitable as an amplifying enzyme. Phosphorylase b is highly abundant in muscle, such as rabbit muscle, and is commercially available. In the absence of AMP phosphorylase b is inactive. In the presence of AMP, AMP binds to phosphorylase b and allosterically activates the enzyme so that it efficiently catalyzes the breakdown of glycogen by phosphorolysis to produce glucose-1-phosphate (G1P). Phosphofructokinase from eukaryotes is activated by AMP, ADP, and 3',5'-cyclic AMP, and phosphofructokinases from prokaryotes *Escherichia coli* and *Bacillus stearothermophilus* are activated by ADP and GDP; isocitrate dehydrogenase is allosterically activated by AMP; and pyruvate kinase is allosterically activated by fructose 1,6-diphosphate (A. Fersht, Structure and Mechanism in Protein Science, 1999, W.H. Freeman and Company).

With particular attention to FIG. 2A, in the case where the product of the primary reaction inhibits the amplifying enzyme 50, the amplified heat 54 occurs when the primary enzymatic reaction does not take place. Thus, in the case of inhibition, an amplified signal occurs when the primary enzyme 50 is inactive. So, for example, in performing common mode rejection, the amplifying enzyme would be placed on the reference side as well as the measurement side, thereby providing a differential signal when the primary enzyme is active and inactivates the amplifying enzyme.

Figure 3:
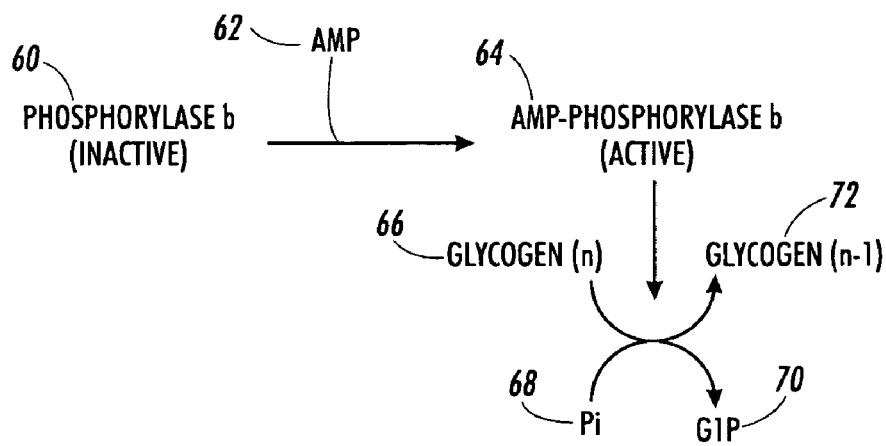
FIG. 3 is a schematic of an amplification reaction for the amplifying enzyme phosphorylase b.

Turning now to FIG. 3, a schematic of the amplifying portion of the preceding enzymatic reaction of FIG. 2A involving phosphorylase b 60 is depicted. AMP 62 binds with inactive phosphorylase b 60 to form active AMP-phosphorylase b complex 64. The active AMP-phosphorylase b complex 64 catalyzes the removal of a terminal glucose residue from glycogen 66. Specifically, the active AMP-phosphorylase b complex 64 catalyzes the reaction of glycogen 66, having n glucose units, and inorganic phosphate ($P_i$) 68 to produce glucose-1-phosphate (G1P) 70 and glycogen 72 having n−1 glucose units. Since the activated complex 64 can turn over many substrate molecules 66 and 68, this reaction is capable of liberating many equivalents of heat per AMP 62 provided. Thus, the enzymatic reaction of activated phosphorylase b with glycogen to produce G1P generates heat sufficient to amplify the heat generated from a primary reaction.

To employ phosphorylase b as the amplifying enzyme, one way is to couple the production of an enzyme-specific product from the primary reaction to the production of AMP. That is, when an enzyme-specific product(s) is used to initiate the downstream reactions and activate the amplifying enzyme, it may be necessary to either convert the enzyme specific product(s) to AMP or convert the enzyme-specific product to a species that may subsequently be converted to AMP through one or more additional reactions. Alternatively, a product other than an enzyme-specific product may be converted to AMP to activate phosphorylase b. The metabolic role of phosphorylase b is to break down glycogen when ATP levels drop and AMP levels rise, supplying glucose to the cell for glycolysis. Glycogen is a polymer of glucose that is used as a storehouse of carbohydrates for short-term energy needs. To perform its function of breaking down glucose, phosphorylase b must be tightly regulated so that glycogen is not degraded unless the cell is starved for energy, i.e., when AMP levels are high. The AMP then acts as a switch to "turn on" or activate or agonize phosphorylase b. To generate the amplified heat from the enzymatic reaction of activated phosphorylase b 64, a sufficient amount of glycogen 66 is provided to react with inorganic phosphate ($P_i$) 68 to form G1P (70) and generate the amplified heat. Preferably, in the activation of phosphorylase b, enzymes that convert AMP to ADP are omitted. Omitting such enzymes prevents AMP from being ultimately recharged to ATP, and thus, AMP is available to activate phosphorylase b.

In the case where a product of the first reaction inhibits the amplifying enzyme, the amplified heat occurs when the primary enzymatic reaction does not take place. Thus, this case gives an amplified signal when the primary enzyme is inactive, which is still a useful "amplification", in the sense that the signal in the presence versus the absence of the primary enzymatic reaction is larger than it would otherwise be.

Any method, means and/or apparatus suitable to monitor chemical reactions by the enthalpy of a reaction as is known in the art may be used with an amplification method as described herein. Preferably, a calorimeter or enthalpy array suitable for detecting heat produced by chemical reactions is used to detect the amplified heat. Of particular usefulness are calorimeters or enthalpy arrays that enable measurement at low volumes, such as volumes less than about 30 microliters, and including ranges of 30 microliters to 50 nanoliters, 1 microliter to 50 nanoliters, as well as 1 microliter or less, or 3 microliters or less, as this reduces the amount of sample required for each measurement. The primary reaction and the secondary reaction cascade are coupled in the apparatus used to detect the heat of the reactions. Generally, prior to performing trials on test materials, i.e., prior to performing the primary reaction coupled with the amplification reaction, the amplification reaction is calibrated in the apparatus device to determine the heat generated by the amplification reaction.

Example 1

Figure 4:
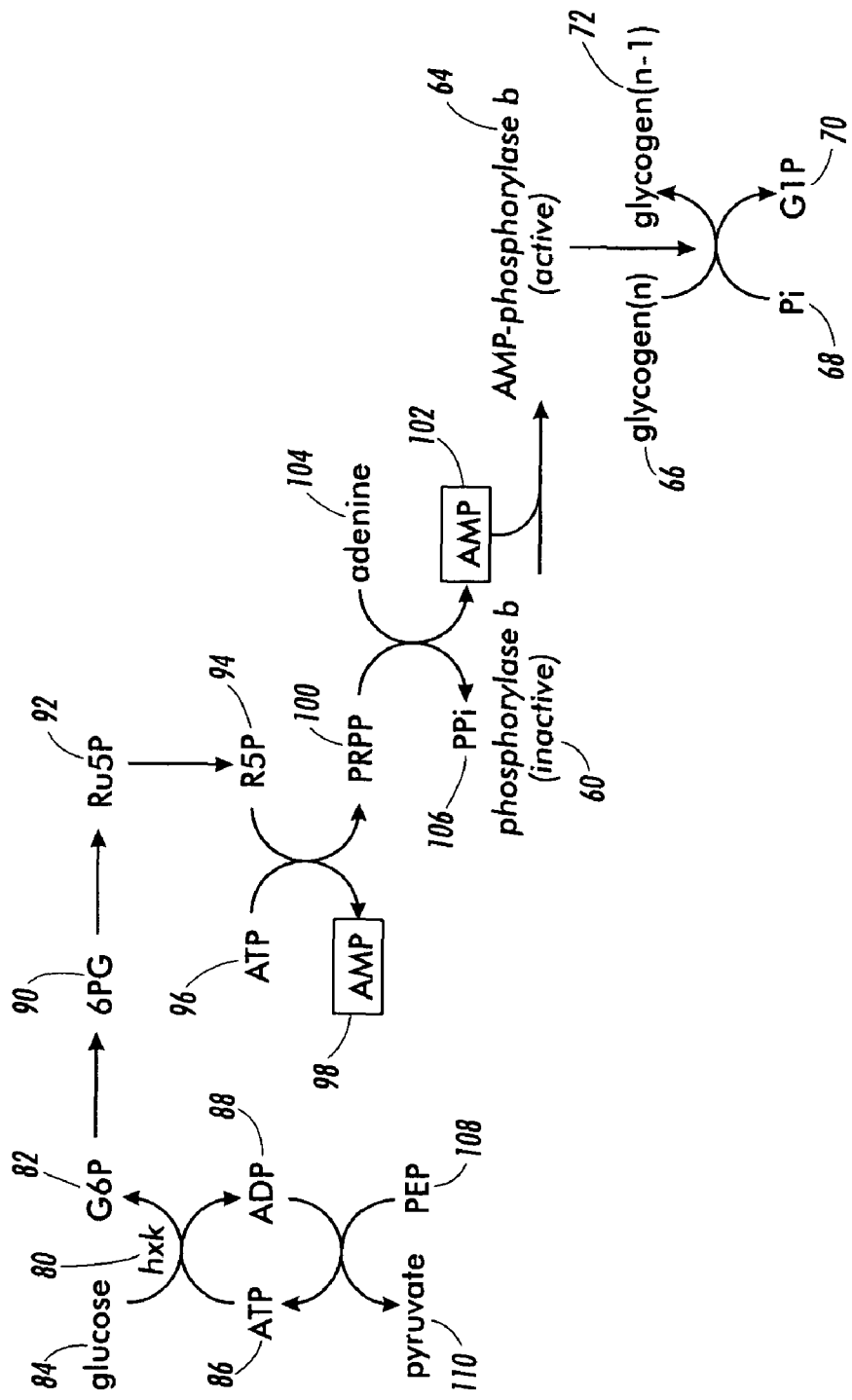
FIG. 4 is a schematic for the amplification of a hexokinase catalyzed reaction, utilizing phosphorylase b as the amplifying enzyme

In this example, a hexokinase catalyzed reaction is amplified using phosphorylase b as the amplifying enzyme. The use of hexokinase as the subject enzyme is to be understood as only an exemplary reference used to illustrate a method of amplification and is not intended to in any manner be seen as a limiting factor of the description. It is to be further understood, therefore, that the methods of amplification as described herein are applicable to studies, using combinatorial techniques and the like, of other substances and drug candidates. The amplification of a hexokinase catalyzed reaction is depicted in the reaction scheme in FIG. 4. Hexokinase catalyzes the phosphorylation of glucose and other sugars. The phosphorylation produces heat, but at low concentrations of enzyme and/or substrate, the heat generated may be too low to detect at a sufficient signal-to-noise ratio using a desired calorimetric method. That is, the heat may not be sufficient enough to provide for an adequate level of precision (of detection). For example, the amount of heat produced may be too low in some applications for detection by enthalpy arrays, yet the use of such arrays would allow combinatorial screening for agonists or inhibitors in a drug development activity. The hexokinase catalyzed reaction in FIG. 4 is for the phosphorylation of glucose. Hexokinase (hxk) 80 catalyzes the phosphorylation of glucose to produce a hexokinase-specific product, namely, glucose-6-phosphate (G6P) 82. Specifically, hexokinase 80 catalyzes the reaction of glucose 84 and ATP 86 to produce G6P 82 and ADP 88. For the enzyme-specific product of the hexokinase reaction to activate the amplifying enzyme, i.e., phosphorylase b, the G6P enzyme-specific product is used to produce AMP. G6P 82 can be used to produce AMP using enzymes from nucleotide metabolism. Generally, G6P 82 is converted to ribose-5-phosphate (R5P) 94 in a series of reactions. Specifically, G6P 82 is converted to 6-phosphogluconate (6PG) 90 by G6P hydrogenase. 6PG 90 is then converted to riboulose-5-phospate (Ru5P) 92 by phosphoriboisomerase, and Ru5P 92 is converted to ribose-5-phosphate (R5P) 94 by phosphoriboisomerase. Activation of ribose-5-phosphate by phosphoribosylpyrophosphate (PRPP) synthase consumes a molecule of ATP 96 to generate a molecule of AMP 98 and PRPP 100. PRPP 100 may then be converted to AMP 102 using adenine ribosyl transferase to generate a second molecule of AMP 102. Thus, the net reaction is that one molecule of G6P 82, ATP 86, ATP 96, and adenine 104 are converted to two molecules of AMP 98 and 102, and a pyrophosphate (PPi) 106. The reaction depletes itself as soon as the ATP is consumed. It is possible to drive the reaction to completion by recycling ADP 88 produced by hexokinase using pyruvate kinase. Pyruvate kinase catalyzes the reaction of phosphoenolpyruvate (PEP) 108 and ADP 88 to yield pyruvate 110 and regenerate ATP 86. A large excess of phosphoenolpyruvate can be used to drive the entire process toward AMP production. In some embodiments, it may be advantageous to omit the enzyme that converts AMP to ADP. Omitting this enzyme prevents the AMP from being regenerated ultimately to ATP and ensures that AMP is available to activate phosphorylase b. All of the enzymes used in the conversion of G6P 82 to AMP 102 and 98 may be purchased or are readily over expressed in *E coli*. The enzymes are stable in solution for days. Further, the AMP generation module is easily grafted onto the hexokinase assay to directly couple AMP production to phosphorylation of glucose.

The production of AMP 102 and 98 activates phosphorylase b 60 and, in the presence of glycogen, the amplification reaction depicted in FIG. 3 occurs. Glycogen 66 is provided as a substrate for the activated AMP-phosphorylase b complex 64. The enzymatic reaction of active phosphorylase b 64 and glycogen 66 converts glycogen(n) 66 to glycogen(n−1) 72 and glucose-1-phosphate (G1P) 70 (as shown in FIGS. 3 and 4) and thereby generates heat. That is, the activation of phosphorylase b initiates the degradation of glycogen into G1P. The heat generated from the enzymatic reaction of phosphorylase b and glycogen amplifies the heat produced from the primary reaction, i.e., from the phosphorylation reaction catalyzed by hexokinase. The heat signal is amplified because the amplifying enzyme, activated AMP• phosphorylase b, catalyzes many reaction events in the time it takes hexokinase, i.e., the subject enzyme, to catalyze one event.

Figure 5:
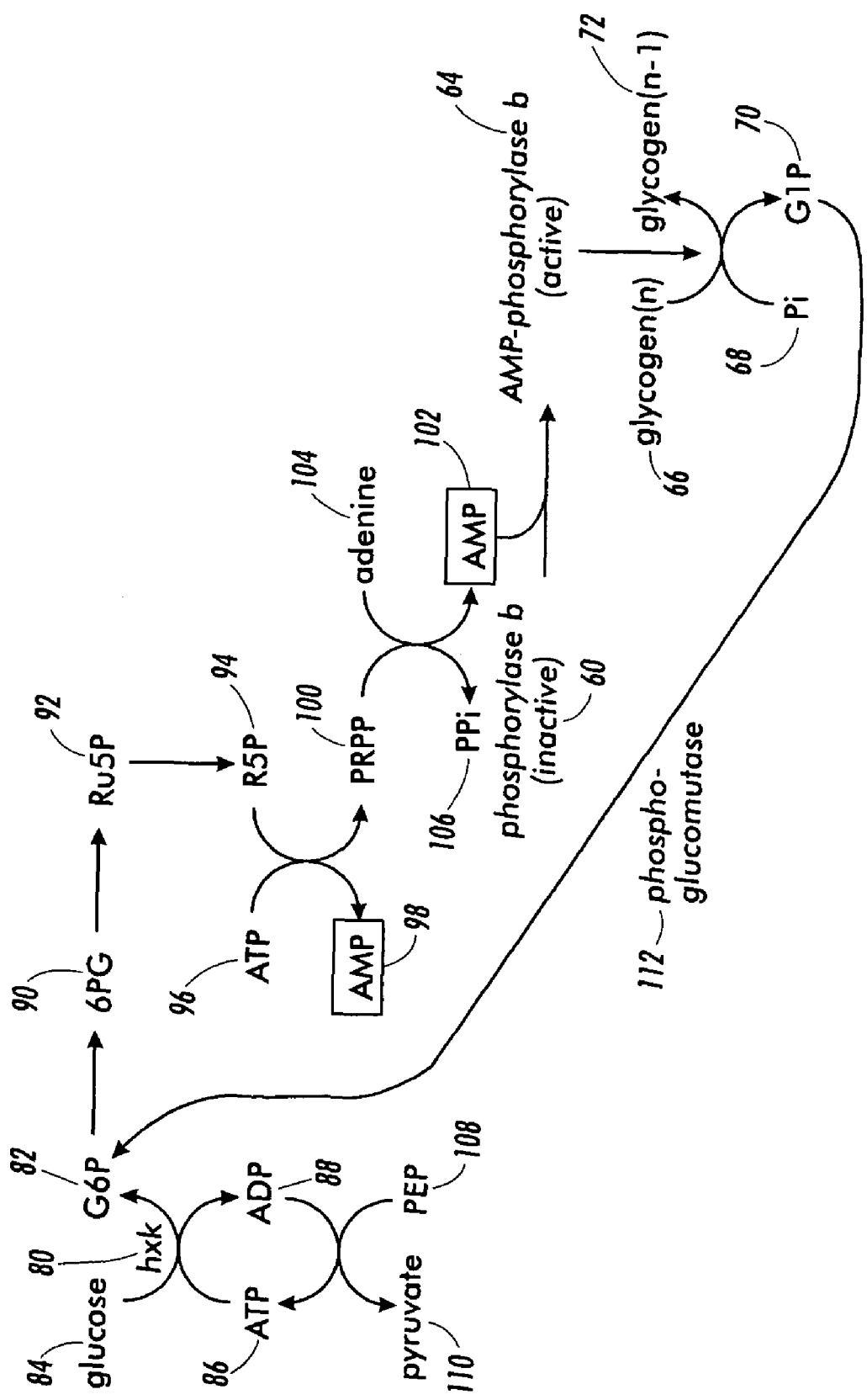
FIG. 5 is a schematic for the amplification of a hexokinase catalyzed reaction using phosphorylase b and a positive feedback loop to amplify the reaction.

In another embodiment of an amplification scheme using phosphorylase b to amplify the heat from a hexokinase catalyzed reaction (FIG. 5), a positive feedback loop is provided to further stimulate the production of AMP and further activate phosphorylase b. In the embodiment of FIG. 5, the positive feedback loop includes converting a product of the amplification reaction, namely G1P 70 to G6P 82 by phosphoglucomutase 112. G6P 82 stimulates the production of AMP 102 and 98 as shown in FIG. 4, and AMP 102 and 98 activates phosphorylase b. Sufficient pools of enzyme, substrate(s) and other compounds are provided to drive the reactions forward. For example, sufficient amounts of enzymes are provided for the conversion of G6P to AMP. Further, the pool of glycogen, or other substrate for phosphorylase b, is kept large to further drive the amplification reaction.

The magnitude of the amplification by the AMP-phosphorylase b activated complex 64 is estimated based on the activity of phosphorylase b. The activity of phosphorylase b is reported to be 30 Units per mg of protein (1 Unit=1 micromole/min). The molecular weight of the protein is 100 kD, so the activity of the protein is effectively around 3000 Units per micromole. Because two (2) AMP are generated for every glucose, every Unit of hexokinase activity can be converted into 6000 Units of phosphorylase b activity. The actual amplification of the hexokinase heat of reaction depends on the enthalpy of glycogen phosphorolysis. If the enthalpy of glycogen phosphorolysis is small, the gain in sensitivity will be diminished. Further, feedback inhibition of phosphorylase b by products of the reactions, including ATP, G1P and G6P, may diminish the amplification. The system will be self-limiting by consumption of a limiting reagent or by product inhibition.

Example 2

Figure 6:
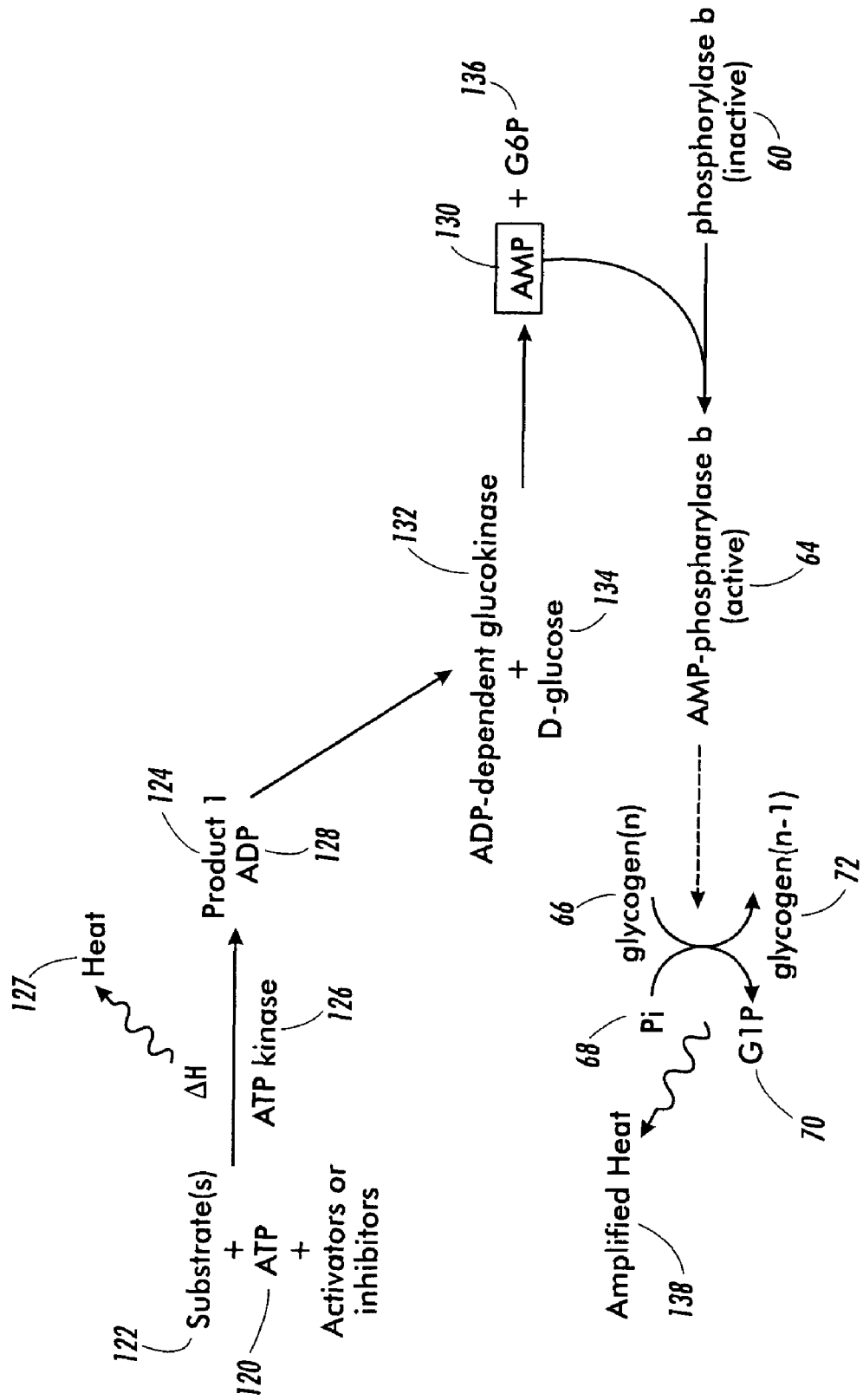
FIG. 6 is a schematic for the amplification of an ATP kinase catalyzed reaction using ADP-dependent glucokinase as the amplifying enzyme.

The amplification scheme shown in FIG. 6 depicts a method for amplifying a signal by using a product other than an enzyme specific reaction product of the primary reaction to initiate amplification. Specifically, the amplification scheme depicts an amplification that is applicable to a broad class of enzymes, the class being ATP kinases in this case. In contrast, the amplification in Example 1 was specific to reactions that produce G6P 84. The choice of whether to use an enzyme specific reaction product of the primary reaction or another product depends on the application. Amplification using an enzyme-specific product (like G6P 82 in FIG. 4) could be useful, for example, if several reactions are occurring simultaneously and one wants to make sure only a particular reaction is being amplified. On the other hand, amplifying by non-enzyme specific products (like ADP for ATP kinases) provides a method that can be used with, for example, orphan enzymes.

The amplification in FIG. 6 utilizes phosphorylase b as the amplifying enzyme. In the primary reaction, ATP kinases catalyze the reaction of ATP 120 with substrate 122 to form a phosphorylated product, i.e., product 124. ATP kinase 126 cleaves a phosphate from ATP 120 and allows substrate 122 to be phosphorylated. The enzymatic reaction involving ATP kinase 126 produces a kinase-specific phosphorylated product 124 and ADP 128. Each phosphorylation event produced by ATP kinase 126 generates a specific amount of heat 127. In certain cases the rate of reaction may be too low, such that the heat produced by the reaction is too low for detection. Where the rate of reaction is too low for detection, it is possible to amplify the heat generation by using ADP 128 rather than the kinase-specific phosphorylated product 124.

ADP 128 is used to initiate the downstream reactions, i.e., the secondary reaction cascade. To activate phosphorylase b 60, ADP 128 is converted to AMP 130. AMP 130 then allosterically activates phosphorylase by forming AMP-phosphorylase b complex 64, which subsequently catalyzes the degradation of glycogen 66, as previously set forth with reference to FIG. 3. Adequate amounts of glycogen 66 are provided to serve as a substrate for phosphorylase b. The activated AMP-phorphorylase b complex 64 catalyzes the breakdown of glycogen 66 and generates heat for each reaction event catalyzed. The heat produced from the catalytic breakdown of glycogen 66 by AMP-phosphorylase b complex 64 amplifies the heat produced from the kinase catalyzed reaction to provide an amount of heat sufficient for detection by an enthalpy array.

Any suitable method may be used to convert ADP to AMP. In the embodiment depicted in FIG. 6, the amplification method employs an ADP-dependent glucokinase as the ADP specific enzyme, and ADP is converted to AMP. In an assay to test an ATP-kinase, D-glucose 134 is provided as the substrate for ADP-specific glucokinase 132 to convert ADP 128 to AMP 130. Specifically, ADP-specific glucokinase catalyzes the reaction of ADP 128 and D-glucose 134 to yield AMP 130 and G6P 136. ADP-dependent glucokinase has an optimum temperature that is high relative to standard testing conditions, but ADP-dependent glucokinase still retains some activity at 25-37° C., typical temperatures for many lab studies. ADP-dependent glucokinase exhibits satisfactory activity at these temperatures to produce AMP and activate the amplifying enzyme phosphorylase b. ADP-dependent glucokinase could be difficult to provide in large quantities, but only enough is needed to provide a sufficient amount of AMP to activate phosphorylase b. Other enzymes may also be used to convert ADP to AMP. Other suitable enzymes to convert ADP to AMP include, but are not limited to, ADP-specific phosphofructokinase and nucleoside diphosphatases. If a nucleoside diphosphatase is used, the nucleoside diphosphatase must be specific to ADP (rather than ATP). The nucleoside diphosphatase converts ADP and water ($H_2O$) to AMP and phosphate. AMP is then utilized to activate an amplifying enzyme like phosphorylase b to react with glycogen and generate amplifying heat 138. A suitable nucleoside diphosphatase is nucleoside disphosphatase from the parasitic protozoon *Entamoeba histolytica*. (J. McLaughlin, D. G. Lindmark, and M. Muelle, Biochem Biophys. Res. Commun. 1978, 82: 913-920).

Example 3

The amplification processes illustrated above may also use a phosphofructokinase to amplify the heat signal of a primary enzymatic reaction. In the primary reaction, the subject enzyme is a GTPase, such as a Ras or G-protein. A GTPase hydrolyzes GTP to GDP using water. GDP then allosterically activates a phosphofructokinase from the prokaryotes *Escherechia Coli* and *Bacillus stearothermophilus*. (A. Fehrst, Structure and Mechanism in Protein Science, pg. 360 (W.H. Freeman & Co. 1999)). Substrates for phosphofructokinase, namely ATP and fructose-6-phosphate, are provided. The heat generated from the reaction of phosphofructokinase with ATP and fructose-6-phosphate produces amplified heat. ADP is produced from the reaction of the phosphofructokinase with ATP and fructose-6-phosphate. ADP will also activate or agonize the phosphofructokinase. ADP activation/agonization of the phosphofructokinase has a swamping effect on the GDP activation. Thus, in an amplification scheme utilizing phosphofructokinase, ADP must be consumed to prevent this swamping effect. An ADPase or an ADP-dependent kinase may be provided as a means for consuming ADP.

Example 4

In this example, the present embodiments are used to study the binding of a ligand, in this case an agonist, to a GPCR. The method can readily be applied to inverse agonists, antagonists, or any other allosteric or competitive modulators as well. GPCRs are one of the most important classes of protein targets for the pharmaceutical industry. GPCRs are membrane proteins involved in signaling cells based on extracellular signaling molecules, and approximately 50% of the top 200 drugs currently on the market target GPCRs. In addition, as a consequence of the completion of the human genome, many GPCRs are being identified from the genome without prior knowledge of their role in cellular pathways, making drug screening of these "orphan" GPCRs difficult. Currently, methods for screening for ligands of orphan GPCRs use cellular assays that involve fluorescent tagging, hypotheses about cellular behavior of the GPCRs, and possibly modifying the GPCR itself, e.g. to make it constitutively active. These methods do not directly detect ligand binding to a GPCR or the associated G-protein activity; rather, they probe cellular responses of pathways signaled by the GPCR. This example illustrates the use of the present invention to directly detect the abovementioned ligand binding.

Ligand binding to GPCRs could in principle be screened generically using nanocalorimeter arrays to measure the heat of binding of ligand to the GPCR, but it can be very difficult to prepare GPCRs at concentrations high enough to detect the heat from binding of ligands. For example, a suspension of membrane fragments with over-expressed GPCR may be about 1 mg membrane protein/ml or less at a viscosity low enough to be suitable for use with nanocalorimeter arrays as described in FIG. 1. The over-expressed GPCR may typically be about 1-2% of the total membrane. Thus, the GPCR concentration is about 0.01 to 0.02 mg/ml or less. For a nominal GPCR molecular weight of 30K Dalton (the number will vary from one GPCR to another), the molar concentration is 0.2 to 0.4 µM or less, which is less than the nanocalorimeter arrays in FIG. 1 can easily measure. Even if a measurement is feasible at higher concentrations of GPCR, reducing the concentration and volume of GPCR samples is also important because preparation of overexpressed GPCR samples is costly and time consuming, limiting the amount of material available for a series of measurements. Thus, there are many advantages to a method that uses small volumes and low concentrations (about 0.01 to 0.10 mg/ml or less) of GPCR.

We have measured reactions involving agonist binding to a GPCR (G-protein coupled receptor), at low GPCR concentration, by using the associated G-protein hydrolysis of GTP as the source of the amplified heat of reaction. Most of the heat in this example is from GTP hydrolysis by G-proteins activated by a GPCR with a bound agonist. GPCRs are transmembrane proteins that bind a receptor (e.g. agonist or inhibitor) on the extracellular side and, upon receptor binding, cause a G-protein (also a membrane protein) on the intracellular side to exchange GDP for GTP. After binding GTP, the G-protein dissociates from the GPCR, and the α subunit dissociates from the β-γ complex. The α subunit and β-γ complex can then migrate independently along the membrane and interact with targets. The α subunit can also hydrolyze GTP to GDP, producing heat, and upon doing so, it recombines with the β-γ complex and becomes inactive again.

Explaining this measurement in terms of FIG. 2A, the GPCR is the primary enzyme 44. We refer to the GPCR as an enzyme because it catalyzes the exchange of GDP for GTP on the G-protein and the subsequent dissociation of the α subunit of the G-protein from the β-γ complex. The G-protein before the GDP-GTP exchange and dissociation can be considered the substrate 40. The GPCR is also a receptor, and as such it is activated in this example by binding of agonist, which is therefore an activator 42. The products 46 of the primary enzymatic reaction are the α subunit and β-γ complex of the dissociated G-protein. In this example, one of the products 46, the α subunit of the G-protein, is also the amplifying enzyme 50. It hydrolyzes GTP, which is the substrate 52, producing the amplified heat 54. The α subunit of the G-protein then recombines with the β-γ complex (not shown in FIG. 2A), making it available again as substrate 40 for the GPCR 44.

In our experiment, we used fragmented membranes containing over-expressed GPCR P2Y6 receptor complex and the associated G-proteins from a baculovirus-inoculated insect cell. Overexpressing the GPCR ensures that the signal we observe is largely due to this GPCR, rather than other GPCRs and GTPases that will also be present in the cell membrane. To prepare the membrane fragments, the membranes were lysed, rinsed twice in buffer, homogenized by two passes through a 26 gauge needle. A Bio-Rad protein assay revealed 100 mg/ml of protein, of which we expect 1-2% to be the P2Y6 GPCR complex of interest. The solution was diluted 100× to a total protein concentration of 1 mg/ml, a suitable concentration for nanocalorimetry measurements using the G-protein amplification method in this example.

We performed a nanocalorimetry measurement using UDP as the agonist. Specifically, on the measurement side of a nanocalorimeter cell (see FIG. 1) we combined a 250 nL drop of the diluted solution of membrane fragments described above with a 250 nL drop of buffer plus UDP and GTP solution, and on the measurement side we combined two 250 nL drops of the buffer solution. The UDP concentration was 0.8 mM, and the GTP concentration was 2.3 mM. As mentioned above, the GTP serves as a substrate for the G-proteins upon agonist binding to the GPCRs. After combining the drops, the concentrations drop accordingly, resulting in the concentrations [UDP]=0.4 mM and [GTP]=1.15 mM, for the combined drop at the point of merging. The amount of P2Y6

GPCR receptor used in this measurement was about 2.5 to 5 ng, corresponding to the 1-2% estimate cited in the previous paragraph.

Figure 7:
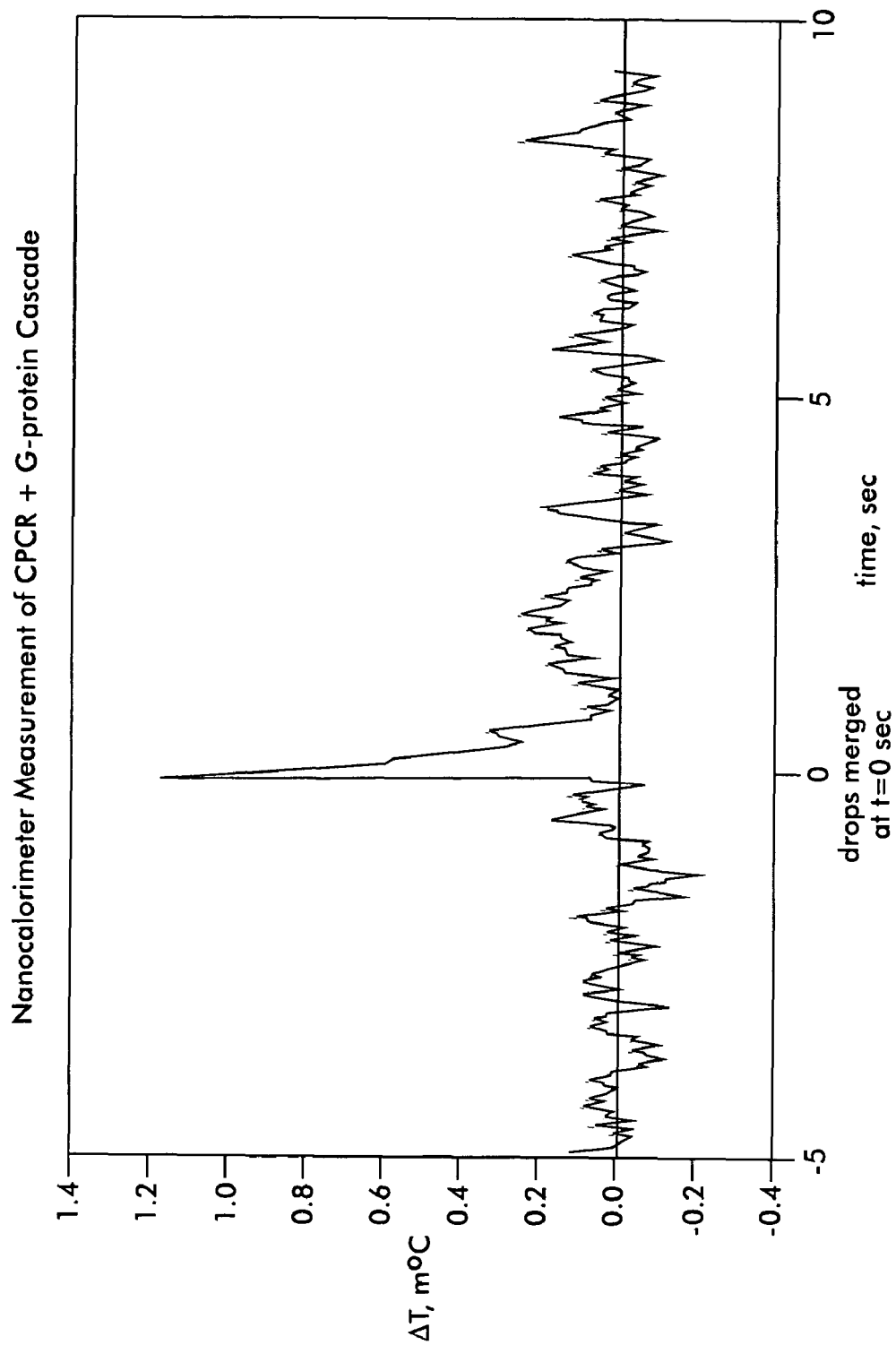
FIG. 7 depicts nanocalorimeter measurements obtained by binding of a ligand to a GPCR.

FIG. 7 shows the results of our nanocalorimeter measurement with these membrane proteins. We see a signal of 1.2 m° C. in magnitude, with duration of about 1-2 of seconds after the drops are merged. FIG. 7 shows that the nanocalorimeter measurement can detect these GPCR binding and G-protein activation cascades. Given the low concentration of GPCR, it follows that much of the heat in FIG. 7 came from GTP hydrolysis in the amplification step. If all of the 1.15 mM GTP were to hydrolyze instantaneously, then the signal would be about 6 m° C. in magnitude, so the observed signal is quite reasonable, considering the finite rate of GTP hydrolysis and the fact that GTP vs. GDP binding to the G-proteins is lessened as the GDP concentration builds up, eventually attenuating the hydrolysis rate. The estimated total amount of receptor complex used in this reaction was 85 femtomoles, an acceptable amount for high throughput screening operations.

In another embodiment, a non-hydrolyzable GTP analog is used on the reference side of the nanocalorimeter, examples of non-hydrolyzable GTP analogs being Gpp(NH)-p (5'-guanylylimidophosphate), GTP-γ-S (guanosine 5'-O-(3-thiotriphosphate)), and AlF4 (which forms a third "pseudo" phosphate on GDP in Gα-GDP). Specifically, one drop on the reference side comprises membrane fragments containing the GPCR of interest, at the same or nearly the same concentration as on the measurement side, along with enough non-hydrolyzable GTP analog to arrest the G-protein activation-deactivation cycle, thereby preventing the hydrolysis of GTP. The second drop on the reference side contains agonist and GTP at the same or nearly the same concentration as the corresponding drop on the measurement side, thereby providing good matching of heats of dilution between the measurement and reference sides when the drops are merged. For illustrative purposes, the agonist in this example is UDP and the GPCR is P2Y6 receptor complex, but one can appreciate that the method illustrated by this example can readily be applied to other GPCRs and their ligand regulators. At the time of the measurement, the two drops on the measurement side are merged (one containing the GPCR of interest and the other containing the agonist and GTP), and at the same time the two drops on the reference side are merged. The differential temperature between the measurement and reference sides is measured, with a temperature rise indicating activation of the GPCR on the measurement side and GTP hydrolysis by the associated G-protein.

In yet another embodiment, a non-agonized suspension of membrane fragments is used on the reference side of the nanocalorimeter. Specifically, one drop on the reference side comprises membrane fragments containing the GPCR of interest, at the same or nearly the same concentration as on the measurement side. The second drop on the reference side contains GTP at the same or nearly the same concentration as the corresponding drop on the measurement side, but it does not contain agonist or test agonist, thereby providing a differential measurement of GTP hydrolysis in the absence versus presence of agonist or test agonist. For illustrative purposes, the agonist in this example is UDP and the GPCR is P2Y6 receptor complex, but one can appreciate that the method illustrated by this example can readily be applied to other GPCRs and their ligand regulators. At the time of the measurement, the two drops on the measurement side are merged (one containing the GPCR of interest and the other containing the agonist and GTP), and at the same time the two drops on the reference side are merged. The differential temperature between the measurement and reference sides is measured, with a temperature rise indicating activation of the GPCR on the measurement side and GTP hydrolysis by the associated G-protein.

In the described embodiments, the methods disclosed herein can be used together with structural studies of GPCRs to discover ligands for GPCRs. As an example of a company pursuing structural studies of GPCRs, Sagres Discovery is working on crystallizing GPCRs and using the crystals to learn more about structure. The objective is to use the structural information to determine candidate ligands. The described embodiments would complement those efforts and speed up the path to finding ligands and leads for GPCRs. For example, structural studies could suggest families of possible ligands, and then nanocalorimeter arrays could be used to screen the family of ligands to find specific instances of ligands, using the amplification described by this invention.

The exemplary embodiments have been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A method of detecting characteristics of an enzymatic reaction of interest comprising:
   initiating a primary enzymatic reaction wherein a product and a first amount of heat are generated in a volume of approximately 30 microliters or less;
   activating an amplifying enzyme that initiates a second enzymatic reaction that produces a detectable amplified amount of heat wherein the product of the primary enzymatic reaction is converted to a species that activates the amplifying enzyme, wherein the species is selected from the group consisting of a substrate for the amplifying enzyme and an agent that causes a covalent modification of the amplifying enzyme;
   measuring the amplified amount of heat; and
   determining, the characteristics of the reaction of interest using the measured amplified heat.

2. The method according to claim 1, wherein the volume is less than 1 microliter.

3. The method according to claim 1, wherein the volume is less than 300 nanoliters.

4. The method according to claim 1, wherein the amplifying enzyme is an ATPase.

5. The method according to claim 1, wherein the amplifying enzyme is activated as a result of covalent modification by a species converted from a product of the primary enzymatic reaction.

6. The method according to claim 5, wherein the activating enzyme is a kinase and the covalent modification comprises phosphorylation of the activating kinase.

7. The method according to claim 1, wherein a succession of enzymatic reaction cascades are used for generation of the amplified amount of heat in a plurality of reactions.

8. The method according to claim 1, wherein the amplifying enzyme is selected from the group consisting of phosphorylases, phosphofructokinases, and isocitrate dehydrogenases.

9. The method of claim 1 wherein the second enzymatic reaction is initiated by a substrate of the amplifying enzyme that was converted from a specie of a product of the primary reaction.

10. The method of claim 9, wherein the specie converted from a product of the primary reaction is ribose-5-phosphate.

11. The method according to claim 9, wherein the amplifying enzyme is activated by a species converted from ADP.

12. A method for monitoring a primary enzymatic reaction comprising: conducting a primary enzymatic reaction wherein a product and a first amount of heat are produced in a volume of 30 microliters or less;

producing a detectable amplified amount of heat by activating an amplifying enzyme that initiates a second enzymatic reaction that produces a detectable amplified amount of heat wherein the product of the primary enzymatic reaction is converted to a specie that activates the amplifying enzyme wherein the specie is selected from the group consisting of a substrate for the amplifying enzyme and an agent that causes a covalent modification of the amplifying enzyme; and detecting the amplified amount of heat.

13. The method according to claim 12, wherein the volume is less than 1 microliter.

14. The method according to claim 12, wherein the volume is less than 300 nanoliters.

15. The method of claim 12, wherein the amplifying enzyme is activated as a result of covalent modification by a specie converted from a product of the primary reaction.

16. The method of claim 15, wherein the activating enzyme is a kinase and the covalent modification comprises phosphorylation of the activating kinase.

17. The method according to claim 12, wherein the amplifying enzyme is selected from the group consisting of phosphorylases, phosphofructokinases and isocitrate dehydrogenase.

18. The method according to claim 12, wherein the second enzymatic reaction further comprises a positive feedback loop.

19. The method according to claim 12, wherein the second enzymatic reaction is initiated by a substrate of the amplifying enzyme that was converted from a specie of a product of the primary reaction.

20. The method of claim 19, wherein the specie converted from a product of the primary reaction is ribose-5-phosphate.

21. A method for monitoring ATP kinase enzymatic reactions, the method comprising:

conducting an ATP kinase enzymatic reaction, the ATP kinase reaction including reacting an ATP kinase with one or more substrates to produce one or more ATP kinase-specific products, the ATP kinase reaction of interest generating a first amount of heat, wherein the ATP kinase and one or more substrates have a combined volume of less than 30 microliters; and activating an amplifying enzyme that initiates a second enzymatic reaction that produces a detectable amplified amount of heat wherein a product of the ATP kinase enzymatic reaction is converted to a species that activates the amplifying enzyme, wherein the species is selected from the group consisting of a substrate for the amplifying enzyme and an agent that causes a covalent modification of the amplifying enzyme; and detecting the heat generated.

22. The method according to claim 21, wherein the ATP kinase is a hexokinase.

23. The method according to claim 22, wherein the substrate is glucose.

24. The method according to claim 22, further comprising a positive feedback loop.

25. The method according to claim 23, further comprising a positive feedback loop.

26. The method according to claim 21, wherein the volume is less than 1 microliter.

27. The method according to claim 21, wherein the volume is less than 300 nanoliters.

* * * * *